US009616188B2

(12) United States Patent
Grasmuck

(10) Patent No.: US 9,616,188 B2
(45) Date of Patent: Apr. 11, 2017

(54) APPARATUS FOR REGULATED DELIVERY OF A GAS, NOTABLY RESPIRATORY ASSISTANCE APPARATUS

(75) Inventor: Gilbert Grasmuck, Saint Gilles (FR)

(73) Assignee: AIRFAN, Colomiers (FR)

( * ) Notice: Subject to any disclaimer, the term of this patent is extended or adjusted under 35 U.S.C. 154(b) by 655 days.

(21) Appl. No.: 14/007,690

(22) PCT Filed: Feb. 24, 2012

(86) PCT No.: PCT/EP2012/000807
§ 371 (c)(1),
(2), (4) Date: Sep. 26, 2013

(87) PCT Pub. No.: WO2012/139681
PCT Pub. Date: Oct. 18, 2012

(65) Prior Publication Data
US 2014/0014109 A1    Jan. 16, 2014

Related U.S. Application Data

(60) Provisional application No. 61/481,454, filed on May 2, 2011.

(30) Foreign Application Priority Data

Apr. 11, 2011 (FR) ...................................... 11 53124

(51) Int. Cl.
*A61M 16/00* (2006.01)
*F04D 25/08* (2006.01)
*F04D 29/58* (2006.01)

(52) U.S. Cl.
CPC ....... *A61M 16/0066* (2013.01); *F04D 25/082* (2013.01); *F04D 29/584* (2013.01);
(Continued)

(58) Field of Classification Search
CPC .. F04D 25/082; F04D 29/5806; F04D 29/584; F04D 29/58; A61M 16/0066; A61M 2205/07; A61M 1/101–1/1036
(Continued)

(56) References Cited

U.S. PATENT DOCUMENTS 2,272,985 A * 2/1942 Smith ........................ A47L 9/22
15/326
2,294,586 A * 9/1942 Troller .................. F04D 25/082
310/63

(Continued)

FOREIGN PATENT DOCUMENTS

FR     2908482        5/2008
FR     2908482 A1 *   5/2008  ........... F04D 25/082
FR     2910081        6/2008

*Primary Examiner* — Valerie L Woodward
(74) *Attorney, Agent, or Firm* — Defillo & Associates, Inc; Evelyn A. Defillo

(57) ABSTRACT

The apparatus (1) includes a fan (2) having a motor (5), an impeller (6) and a fan scroll (7). The motor (5) being contained in a motor casing (8) having a first end connected to the fan scroll (7) and an opposite second end; and a casing (22) receiving the fan (2), defining around that fan (2) a space (23) for flow of gas for cooling the fan (2) having an inlet (24). The first end of the casing (8) includes at least one first hole (10) and the second end of the casing (8) includes at least one second hole (11) separated from the inlet (24) to prevent capture of the hot cooling gas leaving the casing (8) by the inlet (24).

14 Claims, 6 Drawing Sheets

(52) U.S. Cl.
CPC ............... *A61M 2205/3368* (2013.01); *A61M 2205/362* (2013.01); *A61M 2205/3606* (2013.01); *A61M 2205/42* (2013.01)

(58) Field of Classification Search
USPC .................................................. 417/366, 369
See application file for complete search history.

(56) References Cited

U.S. PATENT DOCUMENTS

| | | | | |
|---|---|---|---|---|
| 3,026,808 | A * | 3/1962 | Immovilli | F04D 13/0613 310/63 |
| 3,897,178 | A * | 7/1975 | Palloch | F04D 13/06 417/360 |
| 5,114,309 | A * | 5/1992 | Hengelmolen | F04D 29/30 415/112 |
| 5,350,281 | A | 9/1994 | Hagshenas | |
| 5,491,965 | A * | 2/1996 | Wheeler | B65G 47/91 56/327.1 |
| 5,811,899 | A * | 9/1998 | Warner | A47L 5/22 310/63 |
| 2005/0103339 | A1* | 5/2005 | Daly | A61M 16/0057 128/204.18 |
| 2009/0194101 | A1* | 8/2009 | Kenyon | A61M 16/0057 128/201.22 |
| 2009/0291004 | A1* | 11/2009 | Grasmuck | A61M 16/0066 417/423.14 |
| 2010/0054969 | A1* | 3/2010 | Grasmuck | F04D 25/082 417/371 |
| 2010/0189554 | A1* | 7/2010 | Grasmuck | F04D 25/082 415/198.1 |

\* cited by examiner

APPARATUS FOR REGULATED DELIVERY OF A GAS, NOTABLY RESPIRATORY ASSISTANCE APPARATUS

CROSS REFERENCE TO RELATED APPLICATION

This application is a national stage entry of PCT/EP2012/000807 filed Feb. 24, 2012, under the International Convention claiming priority over French Patent Application No. 1153124 filed Apr. 11, 2011 and U.S. Provisional Patent Application No. 61/481,454 filed May 2, 2011.

FIELD OF THE INVENTION

The present invention concerns apparatus for regulated delivery of a gas, notably respiratory assistance apparatus.

BACKGROUND OF THE INVENTION

It is known to use apparatus for regulated delivery of a gas, notably respiratory assistance apparatus, comprising:

a fan essentially constituted by a motor, an impeller driven by that motor and a fan scroll containing that impeller, the motor being contained in a motor casing having a first end connected to the fan scroll and a second end situated on the side opposite the fan scroll; and a casing receiving the fan, defining around that fan a space for flow of the air for cooling the fan, this space having an air inlet situated at said second end of the motor casing.

Apparatus of this type is described for example in published patent application No FR 2 908 482 in the name of the applicant.

Such respiratory assistance apparatus must be able to operate over a wide range of flow rates, and in particular be capable of delivering a low flow rate of gas (for neonatal or paediatric use). The type of fan motor used in such apparatus, and likewise the fast rotation of that motor, induce high heating of the motor, particularly when the fan is delivering a low flow rate.

This heating is accentuated if the motor casing is closed at said second end by a transverse wall including a lower bearing guiding the shaft of the motor. To prevent flow of air under pressure through this bearing, which would have the effect of drying out the grease in the bearing and polluting the air that has passed through the bearing, this lower transverse wall is solid and completely closes the lower portion of the motor casing, which is not favourable for good cooling of the motor.

Generally speaking, much apparatus of this type suffers from motor cooling problems, which impacts on their performance and their longevity.

SUMMARY OF THE INVENTION

A main object of the present invention is to remedy this essential drawback and consequently to provide apparatus as referred to above having improved performance and increased longevity.

Another drawback of existing apparatus is the risk in the event of overheating of the motor of generating possibly toxic smoke, even polluting the air delivered by the fan, and another objective of the invention is to remedy this drawback.

A further objective of the invention is to facilitate mounting the fan in a casing receiving the fan.

A further objective of the invention is to cool the motor without degrading the operation of the lower bearing of the motor shaft.

The apparatus concerned comprises, in a manner that is known in itself:

a fan essentially constituted by a motor, an impeller driven by that motor and a fan scroll containing that impeller, the motor being contained in a motor casing having a first end connected to the fan scroll and a second end situated on the side opposite the fan scroll; and a casing receiving the fan, defining around that fan a space for flow of gas for cooling the fan, this space having a gas inlet situated at said second end of the motor casing.

According to the invention:

said first end of the motor casing comprises at least one first inlet hole for admission of cooling gas into this casing; and said second end of the motor casing comprises at least one second hole for evacuation of the cooling gas from that casing, the second hole or holes being separated from said inlet of said receiving casing in such a manner as to prevent capture of the hot cooling gas leaving the motor casing by said inlet for admission of cool cooling gas into said space.

Thus the invention comprises in providing simultaneously:

a flow of cooling gas in said space around the fan and thus in particular around the exterior face of the motor casing;

a flow of cooling gas through the motor casing; and evacuation of the hot gas leaving the motor casing, which is clearly separated from the inlet for admission of cool cooling gas into said space, in order to prevent this inlet capturing the hot gas.

There are thus cumulatively provided external and internal cooling of the casing of the motor and cooling of the motor, with clear separation of the inlet for admission of cool gas into said space and the outlet for hot gas that has passed through the motor casing.

Good cooling of the motor of the apparatus is obtained in this way, even at low gas flow rates, enabling improved performance and increased longevity of the apparatus.

Said clear separation also has the decisive advantage, in the event of overheating of the motor, of eliminating the risk of pollution of the gas delivered by the fan to the patient during use of the apparatus for respiratory assistance (this excludes the variant described hereinafter in which the gas is recirculated in the fan scroll).

The aforementioned cooling gas could be constituted of a gas different from the gas delivered by the apparatus, flowing in a dedicated circuit. However, this cooling gas is preferably constituted by a portion of the gas delivered by the apparatus, said first hole or holes communicating with the interior of the fan scroll so that a portion of the gas under pressure delivered by the apparatus passes through said first hole or holes, then passes through the motor casing, and flows to the outside of the motor casing via said second hole or holes.

In this case, in a preferred embodiment of the invention, said first end of the motor casing fits in an opening that the bottom of the fan scroll comprises so that said first hole or each first hole that it comprises opens directly into the fan scroll and is situated immediately below the impeller.

This simplifies the structure of the fan and likewise the mounting of the motor casing on the fan scroll.

The apparatus of the invention preferably comprises a soundproofing casing around said receiving casing and rigidly fastened thereto; this soundproofing casing may comprise a conduit for direct evacuation to the outside of the cooling gas that has passed through the motor casing, toward the exterior, which is suitable if the gas used has no commercial value, in particular if that gas is air; this soundproofing casing may alternatively comprise an orifice or conduit for recirculation of this cooling gas that has passed through the motor casing toward the fan scroll, which is suitable if the gas used has a significant commercial value, in particular if that gas is oxygen.

The fan preferably comprises a sealing part isolating said second hole or holes from said inlet for admission of gas into said space.

This produces perfect separation of the second hole or holes and this gas inlet.

This sealing part may notably take the form of a skirt a first tubular portion of which fits around the peripheral wall of the motor casing, said second hole or holes being arranged outside the area of application of this first tubular portion against this peripheral wall, notably in a transverse end wall that this casing includes.

This second hole or each second hole thus opens onto the interior side of the sealing skirt whereas said inlet to said space is situated on the exterior side of that said sealing skirt.

When the apparatus comprises said soundproofing casing, said sealing skirt comprises a second tubular portion fixed to this soundproofing casing.

Thus the sealing skirt is connected to the motor casing by its first tubular part and to the soundproofing casing by its second tubular part, and in this way enables mounting of the fan in said receiving casing.

This achieves the objective of facilitating mounting of the fan in the receiving casing.

In this case, the sealing skirt preferably comprises an intermediate third tubular portion between said first and second tubular portions and flexibly connecting these first and second tubular portions.

This flexibility enables filtering of vibrations generated by the fan, as much in a direction parallel to the rotation axis of the shaft of the motor as in radial directions relative to that said rotation axis.

This third tubular portion may notably be formed by a thin wall connected to the radially internal wall of said first tubular portion and to the radially internal wall of said second tubular portion.

According to another aspect of the invention, if the fan comprises, at said second end of the motor casing, a bearing guiding the shaft of the motor, the motor casing comprises a covering wall completely covering this bearing and thus eliminating any possibility of the cooling gas passing through this bearing.

This achieves the objective of perfect cooling of the motor without risk of deterioration of this lower bearing.

If the motor shaft is extended beyond a transverse wall that said second end of the motor casing includes, notably to receive a balancing weight, said covering wall is formed by a cap mounted on this transverse wall, covering the whole of the portion of the shaft of the motor that is extended beyond said transverse wall and said bearing.

If said fan scroll comprises a pressurized gas outlet tube, the apparatus preferably comprises a sealing part a first tubular portion around said tube, a second tubular portion whereof is mounted in a soundproofing casing containing said receiving casing, and an intermediate third tubular portion between said first and second tubular portions is connected to these first and second tubular portions.

This sealing skirt also simplifies mounting the fan in the soundproofing casing and filters vibrations generated by this fan.

The casing receiving the fan advantageously has a shape that espouses that of the motor casing and that of the fan scroll so that the wall of this receiving casing is at a substantially constant distance from the wall of this motor casing and the wall of this fan scroll.

An undisturbed flow of the cooling gas in said space is obtained in this way, favouring good cooling of the external side of the wall of the motor casing by forced convection.

BRIEF DESCRIPTION OF THE DRAWINGS

The invention will be clearly understood, and other features and advantages thereof will become apparent in the course of the description with reference to the appended diagrammatic drawings showing by way of nonlimiting example a plurality of possible embodiments of the apparatus for regulated delivery of a gas that it concerns.

DETAILED DESCRIPTION OF THE INVENTION

Figure 1:
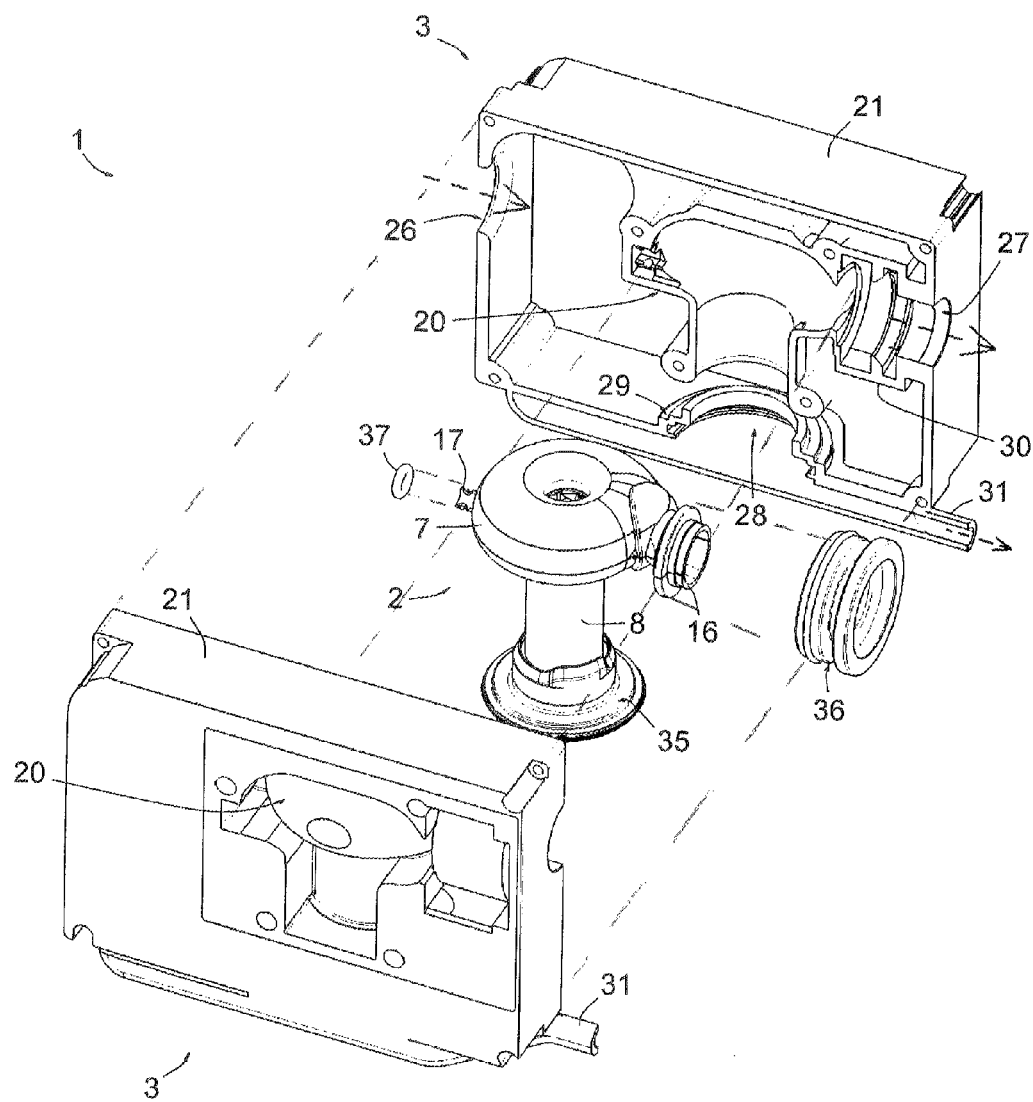
FIG. 1 is an exploded perspective view of the apparatus of a first embodiment.
Figure 2:
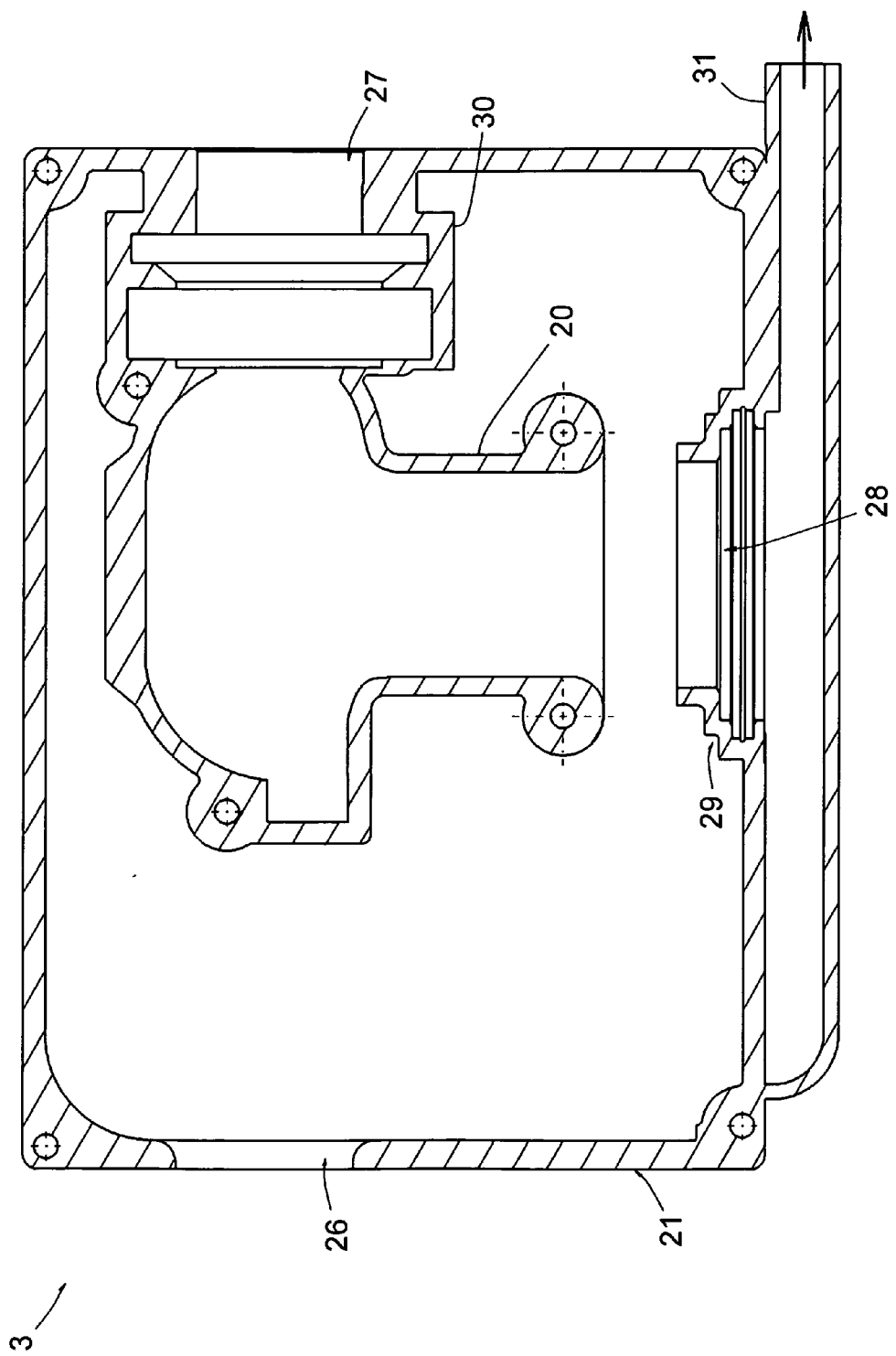
FIG. 2 is a view of a half-casing that this apparatus includes, before fitting a fan that the apparatus also includes.

For simplicity, parts or elements of one embodiment that are included identically or similarly in another embodiment are designated by the same reference numbers.

FIGS. 1 to 4 shows respiratory assistance apparatus 1 comprising a fan 2 and two half-casings 3 adapted to be assembled together around this fan 2.

The fan 2 is essentially constituted by a motor 5, an impeller 6 driven by the motor 5, and a fan scroll 7 containing this impeller 6.

The motor 5 is of cylindrical general shape and comprises an axial shaft on which the impeller 6 is mounted. It is contained in a motor casing 8 have a first end connected to the fan scroll 7 and a second end situated on the side opposite the fan scroll 7. This first end of the casing 8 fits in an opening in the bottom of the fan scroll 7 and is connected to a mounting plate, this mounting plate and this first end comprising a plurality of first holes 10 arranged in a circle concentric with the shaft of the motor 5. Said second end of the casing 8 comprises a transverse wall comprising a plurality of second holes 11 arranged in a circle concentric with the shaft of the motor 5 and comprising a bearing 12 for guiding an extension 13 of this shaft of the motor 5. This extension 13 includes a balancing weight 14 and, like the bearing 12, is entirely covered by a cap 15. The peripheral wall of this cap is situated entirely inside the circle on which the holes 11 are disposed so that it does not cover these holes 11.

The impeller 6 has an axial gas inlet disposed in the inlet of the fan scroll 7, gas flow conduits delimited by the impeller blades, and peripheral outlets.

The fan scroll 7 comprises an axial gas inlet, an annular body and a gas outlet tube 16.

The fan 2 also comprises a lug 17 for registering the fan 2 relative to a receiving casing described hereinafter, this lug 17 being rigidly fastened to the fan scroll 7. This lug 17 has a substantially cylindrical shape and extends radially toward the exterior of the fan scroll 7, being situated at a location diametrically opposite the tube 16.

The two half-casings 3 each form a half-casing 20 receiving the fan 2 and a soundproofing half-casing 21, these half-casings 20 and 21 being, in the example shown, produced by moulding and in one piece. After assembling the two half-casings 3 (see FIG. 4), the two half-casings 20 form a receiving casing 22 for the fan 2 defining, around this fan, a fan cooling gas flow space 23 having a gas inlet 24 situated at said second end of the motor casing 8. The two soundproofing half-casings 21, when assembled, form a soundproofing casing 25 having a gas inlet opening 26, a respiratory assistance gas outlet opening 27, an outlet opening 28 for hot gas for cooling the motor 5, delimited by a structure 29 for mounting the fan 2, a structure 30 for mounting the tube 16, and a conduit 31 for evacuating this hot gas to the exterior of the soundproofing casing 25. This conduit 31 is formed of two demi-conduits moulded in one piece with the two half-casings 3.

Figure 3:
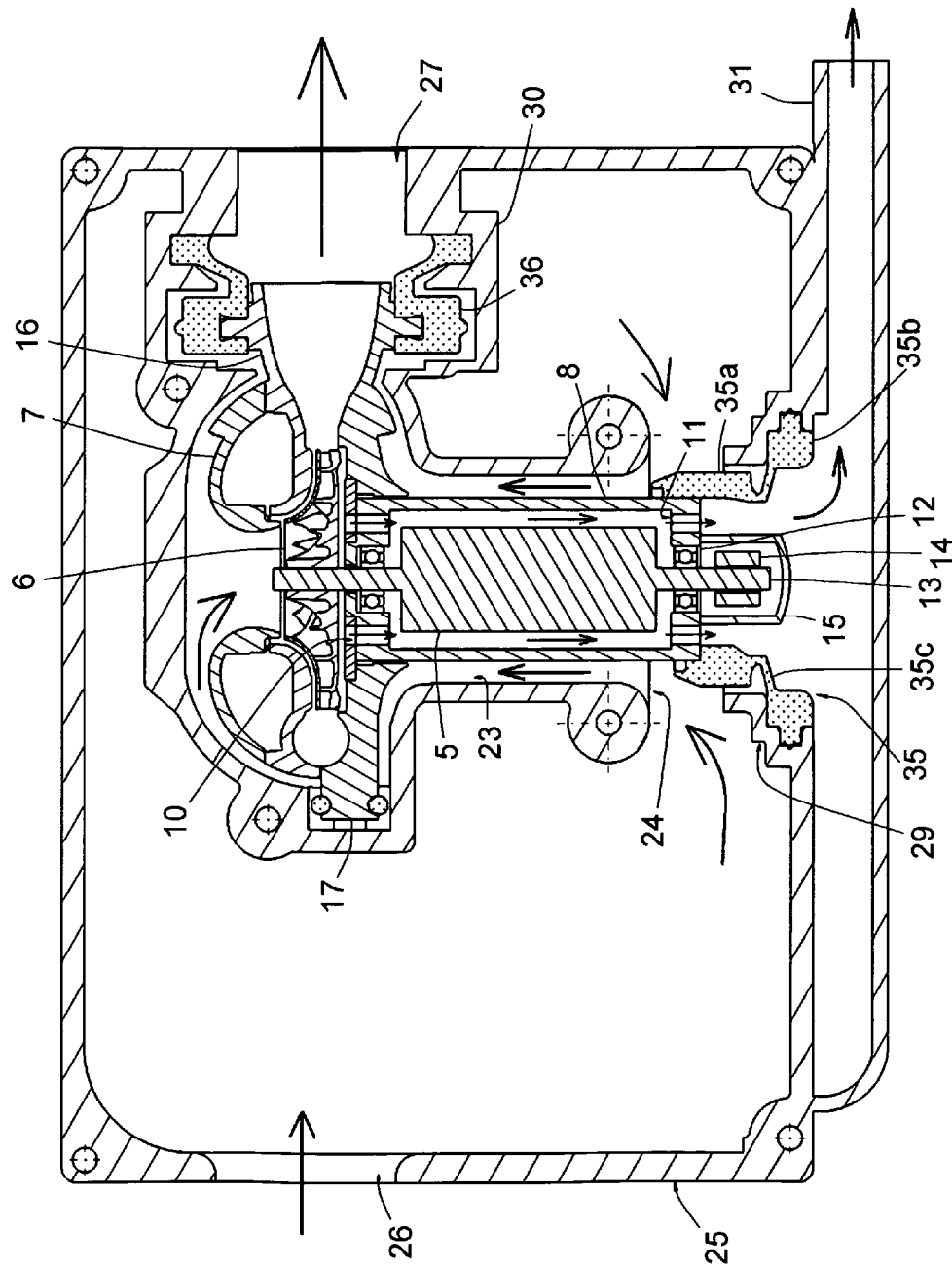
FIG. 3 is a view of the half-casing similar to FIG. 2, after fitting the fan, the arrows showing the circulation of the gas in the apparatus.
Figure 4:
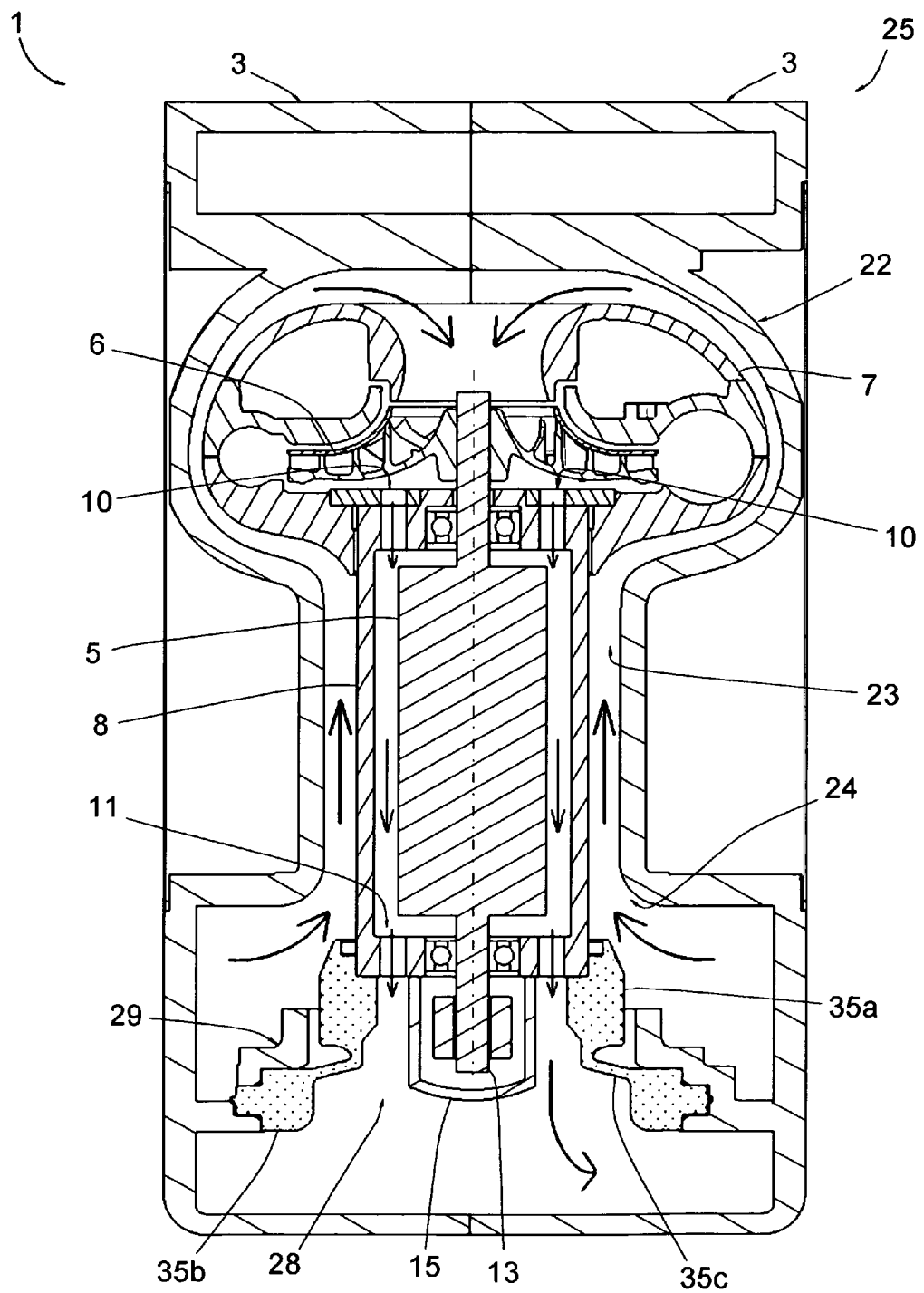
FIG. 4 is a view of the apparatus in cross section through the rotation axis of an impeller that the fan includes, arrows again showing the circulation of the gas in the apparatus.

As FIGS. 3 and 4 show more particularly, the structure 29 for mounting the fan 2 receives an elastomer sealing part 35 taking the form of a skirt. This skirt comprises a first tubular part 35a that fits around the peripheral wall of the motor casing 8, a second tubular part 35b that is a close fit in a lower groove formed by the structure 29, and an intermediate third tubular part 35c between said first and second tubular parts 35a, 35b. This third tubular part 35c is formed by a thin wall connected to the radially internal edge of said first tubular part 35a and to the radially internal edge of said second tubular part 35b and flexibly connects these first and second tubular parts 35a, 35b.

The structure 30 for mounting the tube 16 also receives a sealing part 36 having a structure similar to that of the part 35, with a first portion that is a close fit around the tube 16, a second portion that is a close fit in a receiving groove formed by the structure 30, and a flexible intermediate tubular part.

For its part, the lug 17 receives an O-ring 37 through which it bears against the receiving casing 22, which completes assembly of the fan 2.

With reference to the arrows in FIGS. 3 and 4 showing the routing of the gas in the soundproofing casing 25, the receiving casing 22, and the motor casing 8, the driving of the impeller 6 by the motor 5 in practice causes simultaneously:

a flow of gas in the space 23 around the fan, and thus in particular around the exterior face of the motor casing 8;

a flow of gas through this motor casing 8, entering via the holes 10 and leaving via the holes 11; and evacuation of the hot gas leaving the motor casing 8, which is well separated from the inlet 24 by the sealing part 35, which prevents this inlet 24 capturing any of this hot gas.

These two flows of gas cumulatively enable external and internal cooling of the casing 8 of the motor and the motor 5, with clear separation of the inlet of cool gas into the space 23 and the outlet of hot gas having passed through the casing 8. This achieves good cooling of the motor 5, even at relatively low gas flow rates, improving the performance and increasing the longevity of the apparatus 1.

Said clear separation made possible by the sealing part 35 also has the decisive advantage, in the event of overheating of the motor 5, of eliminating the risk of pollution of the gas delivered by the fan 2 to the patent during use of the apparatus 1 for respiratory assistance.

The sealing parts 35 and 36 for their part facilitate and simplify mounting the fan 2 in the receiving casing 22 and the soundproofing casing 25, with filtering of vibration of this fan thanks to said flexible intermediate portions that these sealing parts comprise.

Furthermore, the cap 15 eliminates all possibility of the cooling gas passing through the bearing 15 and thus eliminates all risk of the grease in this bearing drying out and the gas that has passed through this bearing becoming polluted.

Figure 5:
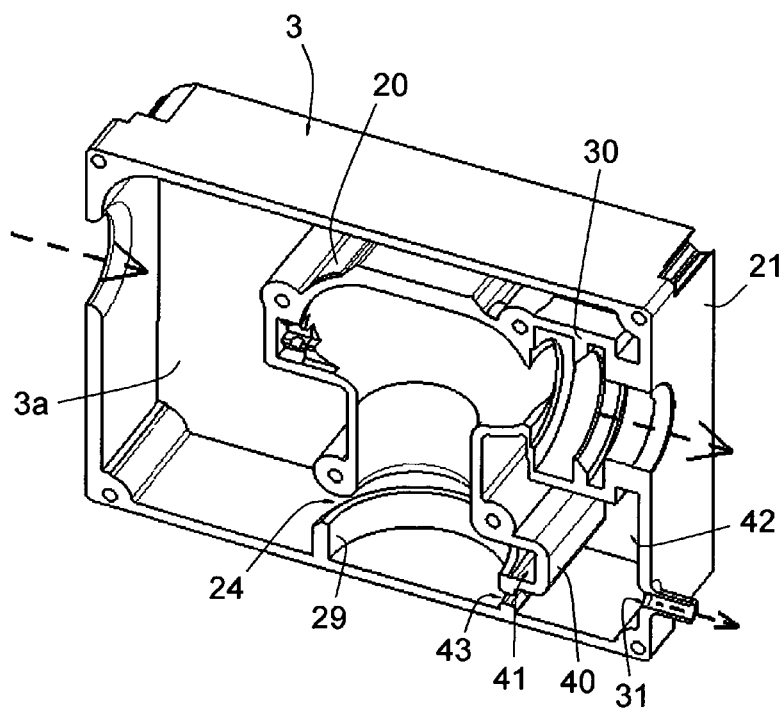
FIG. 5 is a perspective view of a half-casing that the apparatus includes in a second embodiment, before fitting the fan that the apparatus also includes.
Figure 6:
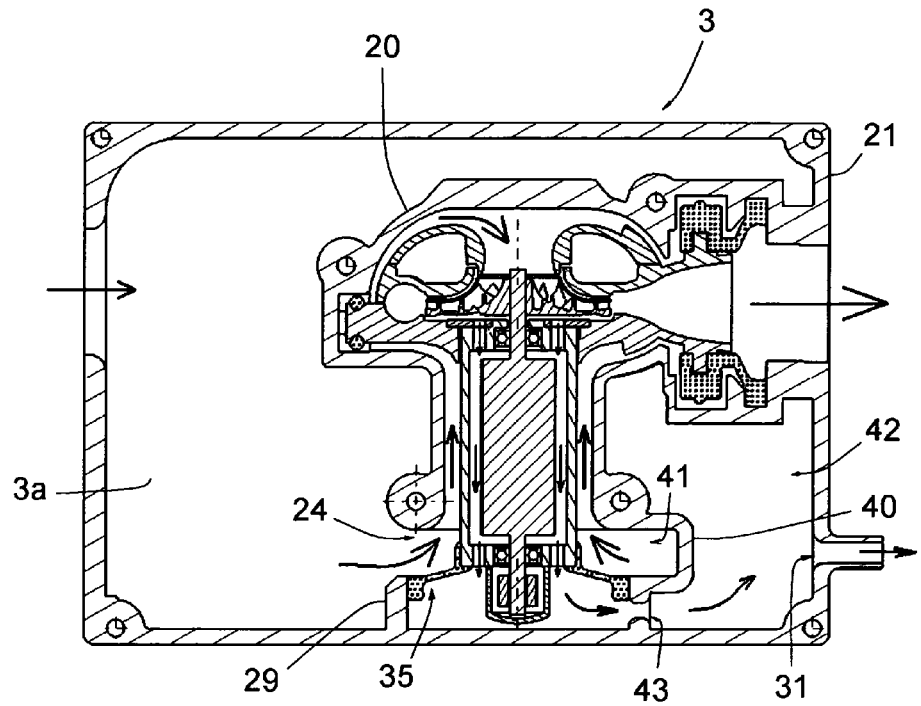
FIG. 6 is a view of this half-casing after fitting the fan, arrows showing the circulation of the gas in the apparatus.

FIGS. 5 and 6 show a second embodiment of a half-casing 3 in which the base of each half-casing 20 is connected to the structure 29 by a transverse wall 40. This wall 40 lies on the side of the half-casing 3 on which is located the structure 30 for mounting the tube 16 and is connected to the back wall 3a of this half-casing 3; it has a "C" profile and, after assembly of the half-casings 3, delimits with these back walls 3a a chamber 41 for capturing the gas aspirated via the opening 24.

Thus the walls 40 of the two half-casings 3 define, after assembly, with the half-casings 20, the walls 3a and the structures 30, a chamber 42 for evacuation of the hot cooling gas. This chamber 42 communicates via an opening 43 with the area delimited internally by the structure 29 and opens to the exterior of the half-casing 3 via an evacuation half-conduit 31.

Accordingly, unlike the first embodiment, the conduit 31 for evacuating the hot cooling gas is integrated into the envelope of the casing formed by assembling the two half-casings 3.

Figure 7:
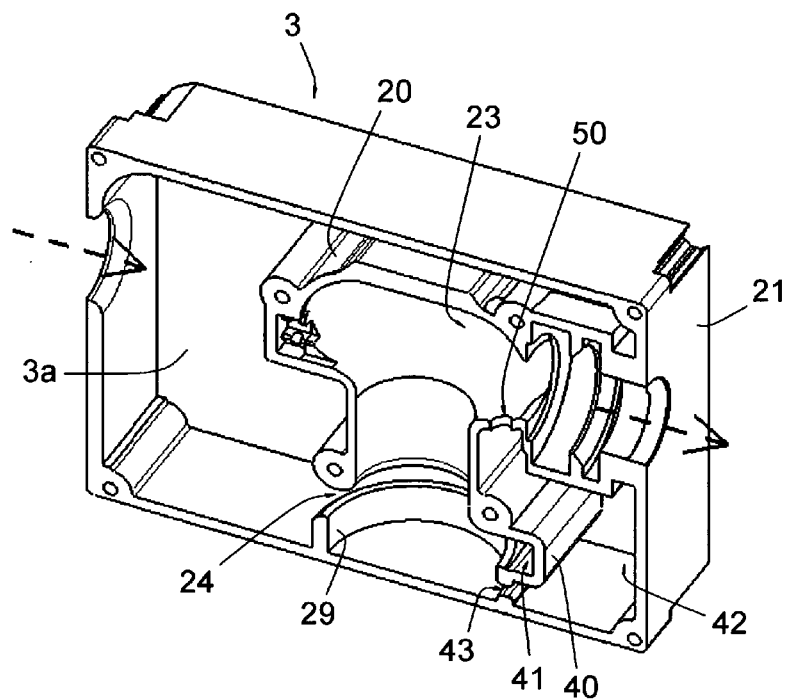
FIGS. 7 and 8 are views respectively similar to FIGS. 5 and 6 of a half-casing of a third embodiment.
Figure 8:
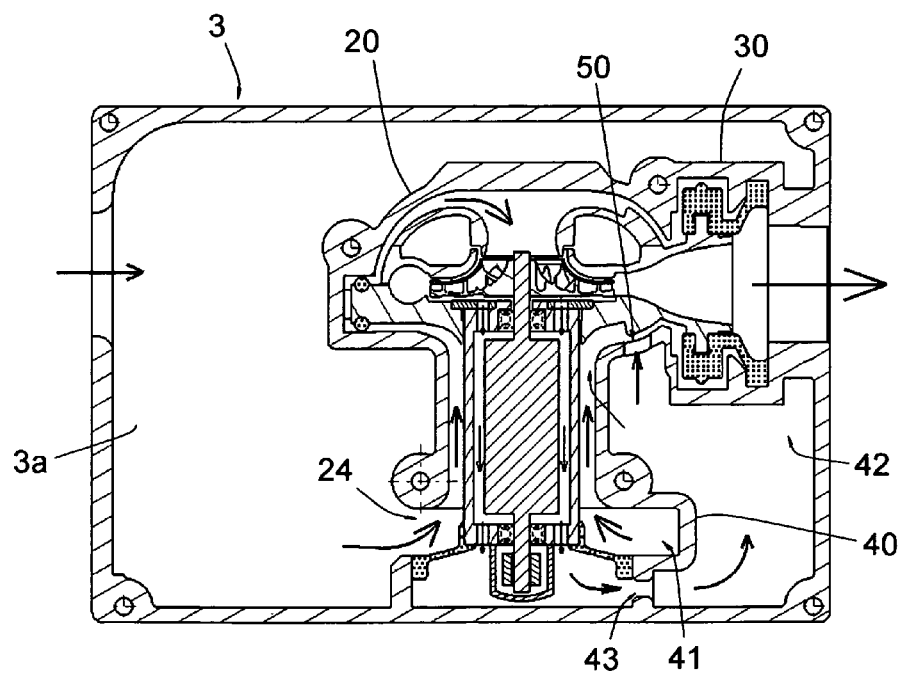

FIGS. 7 and 8 show a third embodiment of a half-casing 3, comprising the wall 40, the chamber 41, the chamber 42 and the opening 43 as described hereinabove. In this third embodiment, the chamber 42 does not open to the outside but communicates with the space 23 in which the gas for cooling the fan flows via an orifice 50. Thus the hot cooling gas is recirculated in the fan scroll 7, which is suitable if the gas delivered by the apparatus 1 has a significant commercial value, in particular if that gas is oxygen (unlike the first two embodiments described, intended rather to function with air). This hot cooling gas is mixed, in very marginal proportions, with cool gas fed via the opening 24, although this does not impact on the degree of cooling of the motor at the gas flow rates usually employed.

As is clear from the foregoing description, the apparatus 1 of the invention has decisive advantages over homologous apparatus of the prior art, described above.

It should be pointed out that this invention has been described hereinabove with reference to an embodiment given by way of example. It goes without saying that it is not limited to that embodiment and that it includes all variations and modifications covered by the appended claims.

The invention claimed is:

1. An apparatus for regulated delivery of a gas comprising:
 a fan including a motor, an impeller driven by the motor, and a fan scroll containing the impeller, the motor being contained in a motor casing having a first end connected to the fan scroll and a second end situated on a side opposite to the fan scroll; and a fan casing for receiving the fan, the fan casing defining around the fan a space for flow of gas for cooling the fan, the space having a gas inlet situated at said second end of the motor casing;

wherein:

said motor casing comprises a peripheral wall around which flows the gas for cooling the fan;

said first end of the motor casing comprises at least one first inlet hole for admission of cooling gas into the fan casing; and said second end of the motor casing comprises at least one second hole for evacuation of the cooling gas from the fan casing, the second hole or holes being arranged in a traverse end wall and separated from said gas inlet of said fan casing to prevent capture of hot cooling gasses leaving the motor casing by said inlet for admission of cooling gas into said space; and wherein the cooling gas is constituted by a portion of the gas delivered by the apparatus, said first hole or holes communicating with the interior of the fan scroll so a portion of the gas under pressure delivered by the apparatus passes through the first hole or holes and then passes through the motor casing and flows to the exterior of the motor casing via said second hole or holes.

2. The apparatus according to claim 1, wherein said first end of the motor casing fits in an opening located at the bottom of the fan scroll so that said first hole or each first hole opens directly into the fan scroll and is situated immediately below the impeller.

3. The apparatus according to claim 1, further comprising a soundproofing casing around said fan casing and rigidly fastened thereto.

4. The apparatus according to claim 3, wherein the soundproofing casing comprises a conduit for direct evacuation to outside of the cooling gas that has passed through the motor casing.

5. The apparatus according to claim 3, wherein the soundproofing casing comprises an orifice or conduit for recirculation of the cooling gas that has passed through the motor casing toward the fan scroll.

6. The apparatus according to claim 1, wherein the fan comprises a sealing part isolating said second hole or holes from said gas inlet for admission of gas into said space.

7. The apparatus according to claim 6, wherein the sealing part takes the form of a sealing skirt a first tubular portion of which fits around the peripheral wall of the motor casing, said second hole or holes being arranged outside the area of application of the first tubular portion against the peripheral wall, in a transverse end wall of the fan casing.

8. The apparatus according to claim 7, wherein said sealing skirt comprises a second tubular portion fixed to the soundproofing casing.

9. The apparatus according to claim 8, wherein the sealing skirt comprises an intermediate third tubular portion between said first and second tubular portions and flexibly connecting these first and second tubular portions.

10. The apparatus according to claim 9, wherein said third tubular portion is formed by a thin wall connected to the radially internal wall of said first tubular portion and to the radially internal wall of said second tubular portion.

11. The apparatus according to claim 1, wherein the fan casing receiving the fan has a shape that espouses that of the motor casing and that of the fan scroll so that the wall of the fan casing is at a substantially constant distance from the wall of this motor casing and the wall of this fan scroll.

12. An apparatus for regulated delivery of a gas comprising:

a fan including a motor, an impeller driven by the motor, and a fan scroll containing the impeller, the motor being contained in a motor casing having a first end connected to the fan scroll and a second end situated on a side opposite to the fan scroll; and a fan casing for receiving the fan, the fan casing defining around the fan a space for flow of gas for cooling the fan, the space having a gas inlet situated at said second end of the motor casing;

wherein:

said motor casing comprises a peripheral wall around which flows the gas for cooling the fan;

said first end of the motor casing comprises at least one first inlet hole for admission of cooling gas into the fan casing;

said second end of the motor casing comprises at least one second hole for evacuation of the cooling gas from the fan casing, the second hole or holes being arranged in a traverse end wall and separated from said gas inlet of said fan casing to prevent capture of hot cooling gasses leaving the motor casing by said inlet for admission of cooling gas into said space;

wherein the fan comprises at said second end of the motor casing, a bearing guiding a shaft of the motor, wherein the motor casing comprises a covering wall completely covering the bearing and thus eliminating any possibility of the cooling gas passing through this bearing.

13. The apparatus according to claim 12, wherein the shaft of the motor whereof is extended beyond a transverse wall on said second end of the motor casing to receive a balancing weight, wherein said covering wall is formed by a cap mounted on the transverse wall, covering the whole of the portion of the shaft of the motor that is extended beyond said transverse wall and said bearing.

14. An apparatus for regulated delivery of a gas comprising:

a fan including a motor, an impeller driven by the motor, and a fan scroll containing the impeller, the motor being contained in a motor casing having a first end connected to the fan scroll and a second end situated on a side opposite to the fan scroll; and a fan casing for receiving the fan, the fan casing defining around the fan a space for flow of gas for cooling the fan, the space having a gas inlet situated at said second end of the motor casing;

wherein:

said motor casing comprises a peripheral wall around which flows the gas for cooling the fan;

said first end of the motor casing comprises at least one first inlet hole for admission of cooling gas into the fan casing; and said second end of the motor casing comprises at least one second hole for evacuation of the cooling gas from the fan casing, the second hole or holes being arranged in a traverse end wall and separated from said gas inlet of said fan casing to prevent capture of hot cooling gasses leaving the motor casing by said inlet for admission of cooling gas into said space;

wherein said fan scroll comprises a pressurized gas outlet tube, comprising a sealing part, a first tubular portion around said tube, a second tubular portion mounted in a soundproofing casing containing said fan casing, and an intermediate third tubular portion between said first and second tubular portions connected to the first and second tubular portions.

* * * * *